(12) United States Patent
De Boer et al.

(10) Patent No.: US 8,450,703 B2
(45) Date of Patent: May 28, 2013

(54) METHOD AND SYSTEM FOR IMAGING SAMPLES (75) Inventors: Ruth Wilhelmine Ireen De Boer, Den Bosch (NL); Bernardus Hendrikus Wilhelmus Hendriks, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 652 days.

(21) Appl. No.: 12/678,781

(22) PCT Filed: Jul. 23, 2008

(86) PCT No.: PCT/IB2008/052950
§ 371 (c)(1),
(2), (4) Date: Mar. 18, 2010

(87) PCT Pub. No.: WO2009/016548
PCT Pub. Date: Feb. 5, 2009

(65) Prior Publication Data
US 2010/0214430 A1    Aug. 26, 2010

(30) Foreign Application Priority Data

Jul. 27, 2007  (EP) .................................. 07113337

(51) Int. Cl.
*G01N 21/64*   (2006.01)
(52) U.S. Cl.
USPC .................................. 250/459.1; 250/458.1
(58) Field of Classification Search
USPC .................................................. 250/459.1
See application file for complete search history.

(56) References Cited

U.S. PATENT DOCUMENTS

| 5,127,730 | A | 7/1992 | Brelje | |
|---|---|---|---|---|
| 7,170,675 | B2 | 1/2007 | Brooker | |
| 2003/0095328 | A1 | 5/2003 | Boehm | |
| 2003/0103662 | A1 | 6/2003 | Finkbeiner | |
| 2003/0152490 | A1 | 8/2003 | Trulson | |
| 2005/0118640 | A1* | 6/2005 | Kureshy et al. | 435/7.1 |
| 2005/0121596 | A1 | 6/2005 | Kam | |
| 2007/0160270 | A1* | 7/2007 | Arini et al. | 382/128 |

FOREIGN PATENT DOCUMENTS

| WO | 03050591 A1 | 6/2003 |
|---|---|---|
| WO | 2005080945 A2 | 9/2005 |
| WO | 2008032100 A1 | 3/2008 |

OTHER PUBLICATIONS

Hamada, S. et al "DAPI Staining Improved for Quantitative Cytofluorometry" Histochemistry, 1983, vol. 79, pp. 219-226.
Haroske, G. et al "1997 ESACP Consensus Report on Diagnostic DNA Image Cytometry" Analytical Cellular Pathology, vol. 17, 1998, pp. 189-200.

* cited by examiner

*Primary Examiner* — Marcus Taningco (57) ABSTRACT

The invention provides a method for imaging samples, at least comprising: —staining of a sample with a first marker material and with a second marker material; —utilizing the first marker material in a focusing step for focusing an imaging device with respect to the sample; and —utilizing the second marker material and the imaging device, which has been focused in the focusing step, in an imaging step to acquire an image of the sample. The invention also relates to a system for imaging samples.

14 Claims, 4 Drawing Sheets

METHOD AND SYSTEM FOR IMAGING SAMPLES

The invention relates to a method for imaging samples, and a sample imaging system.

BACKGROUND

Various sample imaging methods are known from the art, for example optical microscopy (both optical reflection and transmission microscopy), fluorescence microscopy, and other methods. For example, the imaging can include scanning imaging or wide field imaging. Also, for example, imaging of samples can be applied to diagnose cancer. A known non-invasive method is to diagnose on samples having only a few cells by applying DNA-cytometry. An overview is provided by G. Haroske, F. Giroud, A. Reith and A. Bocking, in "1997 ESACP consensus report on diagnostic DNA image cytometry", Analytical Cellular Pathology 17 (1998), 189-200. This method is based on the presence of numerical and/or structural chromosomal aberrations (aneuploidy), which are only detectable in tumor (neoplastic) tissue. Detection of DNA-aneuploidy allows the very early diagnosis of cancer, often years ahead of histological diagnoses on biopsies A known DNA sample imaging method uses light of single wavelength. To that aim, the cell nucleus (DNA content) is coloured using a commonly known Feulgen staining method. The colouring step in this method, however, is time consuming, since it is based on a 4.5-hour Feulgen staining process. As a result, performing a brush biopsy and doing a real time measurement on the spot is not possible in this way.

As an alternative, it is known to use a fluorescent DNA staining, for example the marker DAPI that has a high specificity for binding to DNA.

The use of fluorescent DNA staining has certain advantages over Feulgen staining. For example, fluorescence allows for higher sensitivity of measurement than white light absorption. Moreover, most fluorescent dyes have a much faster staining time than the Feulgen staining process; for example, a DAPI-staining can be performed in several minutes.

However, an issue of using a fluorescent DNA dye is the fading of the fluorescence, due to irreversible photobleaching. It is known to use anti-fade agents to slow down the photobleaching to some extent, however, that only reduces the problem, but does not solve it.

Besides, in fluorescence DNA cytometry, focusing of a suitable illumination beam is done using the same light source and detection technique (fluorescence) as during the measurement itself. This will cause uncontrolled photobleaching of the fluorophores, and therefore leads to an increased Coefficient of Variance (CV) in the DNA cytometry measurement.

SUMMARY

The present invention aims to solve the above-mentioned problems. Particularly, an object of the invention is to provide an improved method for imaging samples, and an improved sample imaging system.

According to an embodiment, there is provided a method for imaging samples, the method at least comprising:
staining of a sample with a first marker material and with a second marker material;
utilizing the first marker material in a focusing step for focusing an imaging device with respect to the sample; and
utilizing the second marker material and the imaging device, which has been focused in the focusing step, in an imaging step to acquire an image of the sample.

In this way, the imaging device can be focused with respect to the sample using the first marker material, wherein subsequently an accurate measurement (imaging) of the sample can be achieved by the imaging device using the second marker material.

For example, focusing of the imaging device can involve setting the imaging device such that the device can take a sharp image of the sample, and particularly of a predetermined sample part, for example one or more sample components or sample structures, for example one or more of: a molecule, nucleic acid, DNA, RNA, antibody, a cell, a cell part, a membrane, protein, tissue, and biologic material. In other words, focusing can involve bringing one or more imaging units of the imaging device and the sample into a certain in-focus arrangement with respect to each other, so that the imaging device can acquire a desired in-focus image of the sample (or sample part).

The method can include determining a plurality (for example sequence) of in-focus positions, for example relating to different sample parts, as part of the focusing step, leading to in-focus information containing those in-focus positions. The resulting in-focus information can then be used in an imaging sequence, involving the focusing of the imaging device with respect to the sample (or sample part) to each in-focus position and to obtain the image of the sample (or sample part) at the respective in-focus position. Alternatively, different sample parts can be imaged subsequently, using a respective focusing step and respective imaging step for one sample part to be imaged, before application of a focusing step and respective imaging step for a next sample part, as will be appreciated by the skilled person.

Preferably, the imaging step involves illuminating the sample during a relatively short predetermined (preferably fixed) time period, for example a period of about 10 seconds or less, particularly 1 second or less, for example during a fraction of a second, for each image to be taken. This is particularly advantageous in case that the illumination of the sample during the imaging (i.e. measurement) step involves degradation (for example photobleaching) of the second marker material due to the second marker material receiving that radiation.

Preferably optical properties of the second marker material differ from optical properties of the first marker material.

For example, the sample can be irradiated to detect the first marker material, in the focusing step, using a first type of (illumination) radiation that does not degrade the second marker material, wherein the sample is irradiated to detect the second marker material, in the imaging step, using a second type of (illumination) radiation that degrades the second marker material.

According to a preferred embodiment, at least the second marker material is a fluorescent marker material (for example a fluorescent dye). In a non-limiting embodiment, the first material and second marker material are fluorescent markers, having different fluorescent properties.

Also, according to a further embodiment, the first marker material and second marker material can be designed to tag the same sample component or sample structure, for example one or more of a molecule, nucleic acid, DNA, RNA, antibody, cell, cell part, protein, a membrane, tissue, and biologic material. The tagging of the sample component can include:

binding to that sample component, interacting with that sample component and/or another type of tagging, as will be appreciated by the skilled person. In this way, precise focusing to that sample component or structure can be carried out by the focusing step, where-after that sample component or structure can be accurately imaged by the imaging step.

The focusing step and the imaging step can involve irradiation of the sample with suitable types of radiation, and detection of resulting sample radiation emanating from the sample using a radiation detector of the imaging device. The mentioned resulting sample radiation can include various types of radiation, depending on the radiation used to irradiate the sample, and on the marker materials, as will be appreciated by the skilled person. For example, radiation emanating from the sample can include one or more of: a reflected part of incoming (illumination) radiation, a transmitted part of incoming radiation, and fluorescent radiation, depending on the sample, sample markers and type of illumination radiation.

For example, radiation used in the focusing step can be specifically suitable to interact with the first marker material such that the imaging device can detect the first marker material, and radiation used in the imaging step can be chosen to interact with the second marker material to detect that second marker material. Advantageously, the same radiation detector is used to detect resulting radiation emitted or transmitted by the sample (i.e. the 'sample radiation'), leading to a compact and accurate imaging system.

An embodiment of the invention provides a sample imaging system, the system comprising an imaging device configured to image samples and a focusing unit configured to focus the imaging device onto samples to be imaged, the system including a controller that is configured to control the system to carry out the focusing and imaging steps of the method according to the invention. Thus, above-mentioned advantages can be achieved.

Further advantageous embodiments of the invention are described in the dependent claims. These and other aspects of the invention will be apparent from and elucidated with reference to non-limiting embodiments described hereafter, shown in the drawings.

DETAILED DESCRIPTION OF EMBODIMENTS

Similar or corresponding features are denoted by similar or corresponding reference signs in this application.

Figure 1:
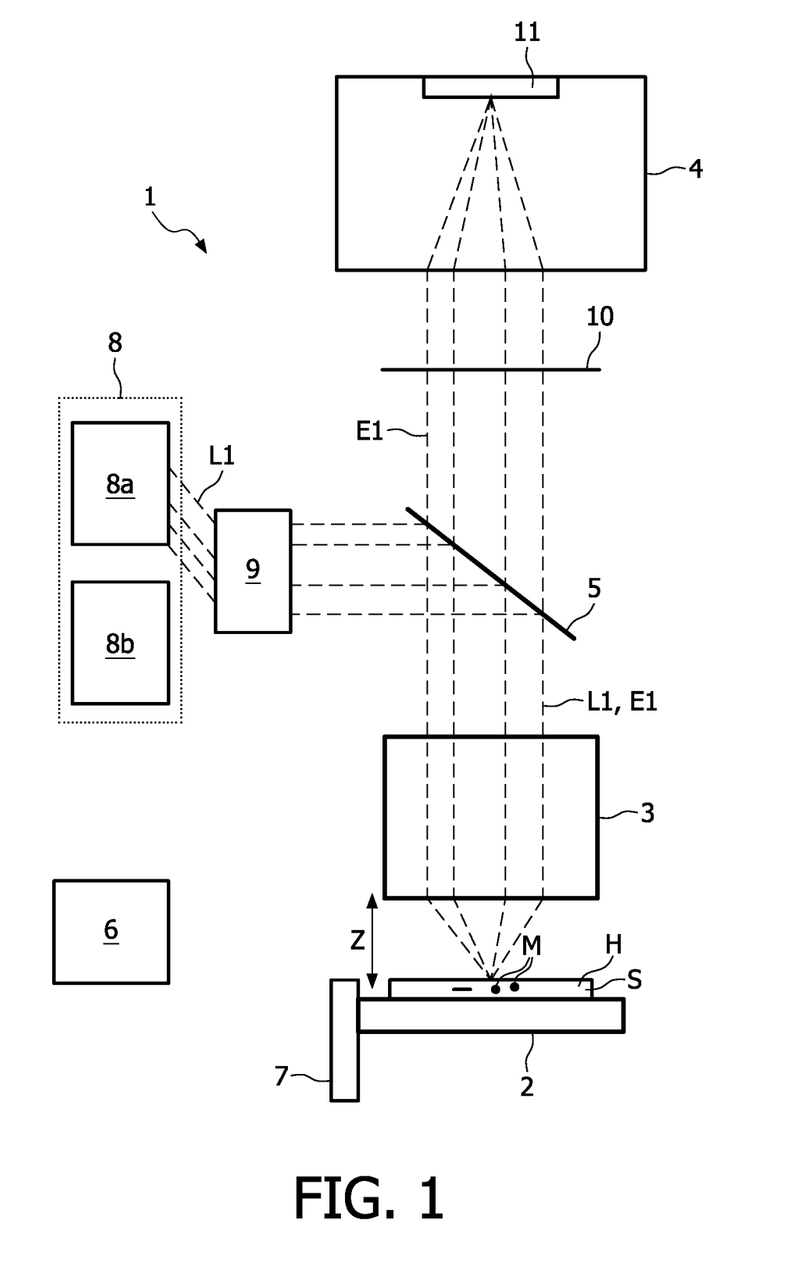
FIG. 1 schematically depicts an embodiment of an imaging system, during a focusing step.
Figure 2:
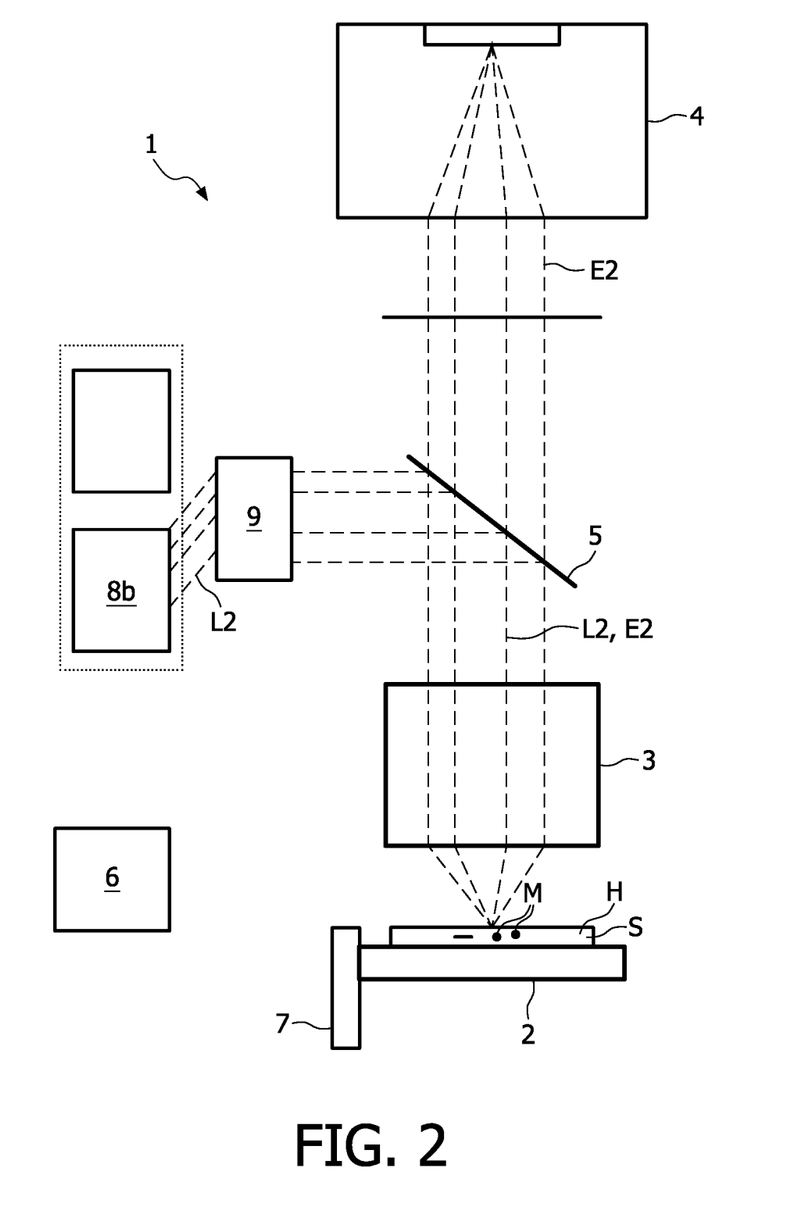
FIG. 2 depicts the embodiment during an imaging step.

FIGS. 1-2 schematically shows a non-limiting example of a sample imaging system. The system comprises an imaging device 1 configured to image samples and a focusing unit 3, 6, 7 configured to focus the imaging device onto samples to be imaged. In the present embodiment the focusing unit 3, 6, 7 is an integral part of the imaging system 1. Radiation beam paths are schematically depicted by dashed lines (L, E) in the drawing.

Particularly, the imaging device 1 is a fluorescence imaging microscope 1, for example a fluorescence scanning microscope, a fluorescence scanning confocal microscope, or a different type of fluorescence microscope, however, the device 1 can also be a different type of imaging device.

The system can include a controller 6, configured to control operation of the system. Particularly, the controller 6 is configured to control the system to carry out certain focusing and imaging steps, as will be explained below. The controller 6 can be configured in various ways, for example comprising suitable hardware and/or software, a data processor, microcontroller, computer and/or other electronics. The controller 6 can at least be configured or programmed to provide controller functionality to carry out mentioned focusing and imaging steps. Besides, the controller can be configured to control system initialization, to provide user interaction (for example via a suitable user interface), for storing imaging data (i.e. sample images), and or for other purposes. The system can include one or more suitable memory devices (for example being part of the controller 6, or being separate therefrom) for storing images, a display (not shown) for displaying detected images, as will be appreciated by the skilled person.

The present imaging device 1 is provided with a support structure 2 configured to hold a sample holder H. The sample holder H can be configured to hold various types of samples S, for example biological samples S, and particularly samples containing certain sample components or sample structures, for example one or more of a molecule, nucleic acid, DNA, RNA, antibody, a cell or cell part, a (cell) membrane, protein, tissue, and biologic material. Said sample components or structures are schematically indicated via arrows M in the drawing. As will be appreciated by the skilled person, the sample holder H can be configured in different ways, for example being made of a material (glass, transparent plastic) that is transparent to the types of illumination radiation and sample radiation E used/present in the method described below.

The present imaging device 1 is provided with an optical system 3 and a radiation detector 4, the optical system 3 being configured to transmit radiation, emitted from a sample S held by the sample holder (at the support structure 2), to the detector 4.

The detector 4 can be configured in various ways, and can include an eye-piece, a photosensor device 11, a camera, imaging means, filter means, data processing means, and/or other suitable detector means. For example, optionally, one or more filters 10 can be provided to filter certain radiation spectrum parts from the radiation upstream with respect to the detector 4, depending on the type of detector used and the radiation that is emitted from the sample S towards the detector during operation.

The imaging device 1 can be focused with respect to the sample S, such that the device 1 can acquire a sharp image of the sample S. As is mentioned above, the focusing can involve bringing one or more imaging units of the imaging device 1 and the sample S into a certain in-focus arrangement with respect to each other, so that the imaging device (particularly the detector unit 4 or sensor 11) can acquire a desired in-focus image of the sample (or sample part).

In the present embodiment, the optical system comprises an objective lens part or unit 3, located opposite the sample support structure 2. In an embodiment, the imaging device 1 is in-focus with respect to a sample S or sample component M (held by holder H at/on the support 2), when a focus plane of the objective lens part 3 intersects the sample S or sample component M, respectively. The objective lens part 3 and sample S can be moved with respect to each other, in a direction indicated by double arrow Z, for focusing the device 1. In the present embodiment, to that aim, a drive mechanism 7, for example including a suitable actuator or motor, is provided, the drive mechanism 7 being configured to move the sample support structure 2 in said direction Z (i.e., a focusing direction of the device 1). Alternatively, the objective lens part 3 can be provided with a suitable actuating mechanism for repositioning that lens part 3 with respect to a sample S. Preferably, the mentioned drive mechanism 7 is controllable by the controller 6.

In a further embodiment, one or more actuators can also be included to scan the sample S (i.e. sample holder H, or support 2) and the lens unit 3 in one or more other directions (particularly directions that are orthogonal to the Z-direction) with respect to each other.

A radiation source assembly 8 is provided to illuminate the sample S. For example, the radiation source assembly 8 can be part of the illumination device 1. In an embodiment, the radiation source assembly 8 can be arranged to illuminate a sample, held on the sample support structure 2, directly. In the present embodiment, radiation emanating from the source assembly 8 is directed to the sample via the objective lens part 3. To this aim, a dichromatic mirror or beamsplitter 5 is provided, arranged downstream with respect to the radiation source assembly 8, and between the detector part 4 and the objective lens unit 3. The dichromatic mirror or beamsplitter 5 can reflect radiation emanating from the source part 8 towards the objective lens part 3, and can transmit sample radiation emanating from the objective lens part 3 towards the detector 4 (as in the drawing). The skilled person will appreciate that the imaging system can be configured in many other ways; for example, the locations of the detector part 4 and source assembly 8, 9 can be interchanged.

Preferably, during use, a sample S to be imaged has been stained by at least a first marker material and a second marker material. Each marker material can interact with suitable incoming radiation L (i.e. illumination-radiation, transmitted by the objective lens unit 3 onto the sample S in this embodiment), for example via absorption, reflection and/or photoluminescence (i.e. fluorescence), to provide or generate or affect resulting sample radiation E (i.e. radiation emanating from the sample S). For example, the interaction can include single-photon excitation, or multi-photon excitation.

According to an advantageous embodiment, both the first and second marker materials are fluorescent marker materials (i.e. fluorophores). Alternatively, one or both marker materials can be (a) non-fluorescent marker material(s), for example radiation absorbing marker material(s) to provide absorption staining of the sample.

Good results can be obtained in the case that the first marker material and second marker material are designed to tag the same sample component or sample structure, for example one or more of: a molecule, nucleic acid, DNA, RNA, antibody, a cell or cell part, a (cell) membrane protein, tissue, and biologic material.

For example, optical properties of the second marker material can differ from optical properties of the first marker material. The first marker material and second marker material can be fluorescent markers, having different fluorescent properties. For example, fluorescence radiation emission peaks of the marker materials can be located at different wavelengths (as in FIG. 4, see below).

Preferably, a main radiation absorption peak of the first marker material does not coincide with (i.e. has a different wavelength than) a main radiation absorption peak of the second marker material.

Figure 4:
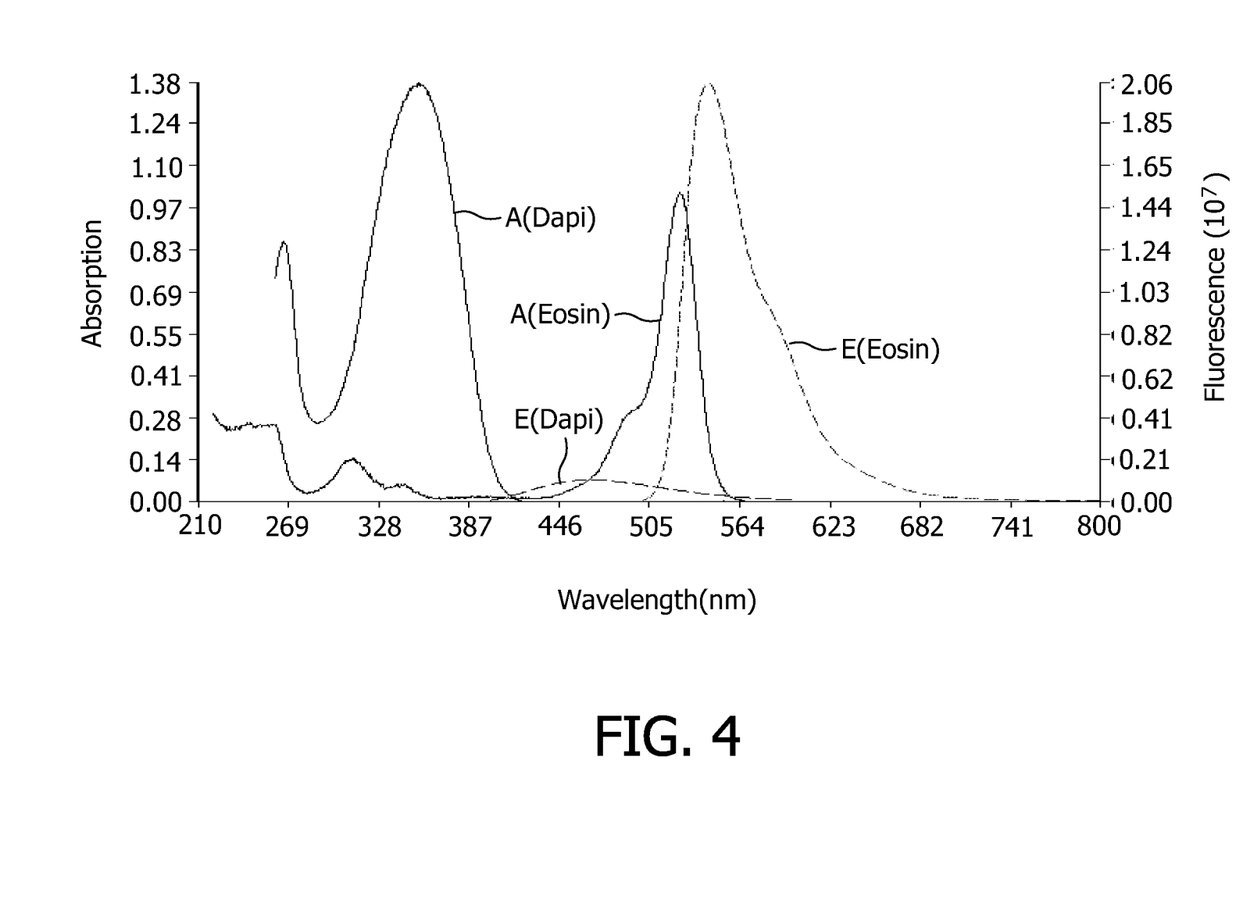
FIG. 4 shows a graph of absorption and emission spectra of two different marker materials, indicating absorption and fluorescence as function of wavelength.

According to an embodiment, the wavelength of a main radiation absorption peak of the first marker material can be located at least 50 nm above or below the wavelength of a main radiation absorption peak of the second marker material, particularly 100 nm, and more particularly 150 nm (as in FIG. 4, see below).

Preferably, the wavelength of a main radiation absorption peak of the first marker material is higher than the wavelength of a main radiation absorption peak of the second marker material, particularly in the case that the first marker material is a fluorescent material. In that case, premature radiation absorption by the second marker material with fluorescence radiation emanating from the first marker material (said fluorescence radiation generally having a lower wavelength than a main radiation absorption peak of the respective fluorescent marker material) can be prevented in a simple manner.

In a non-limiting example, the sample S can be stained using Eosin Y as a first marker material, and with DAPI (4',6-diamidino-2-phenylindole) as a second marker material, or vice-versa. FIG. 4 shows emission and absorption spectra of these marker materials. Therein, A(Dapi) and E(Dapi) indicate the absorption spectrum and emission spectrum, respectively, of DAPI, whereas A(Eosin) and E(Eosin) indicate the absorption spectrum and emission spectrum, respectively, of Eosin Y. The emission spectrum of DAPI has an excitation maximum around 360 nm, and an emission peak at 460 nm; Eosin Y absorbs around 525 nm, and emits at ~550 nm. At the excitation maximum of DAPI, Eosin Y exhibits approximately zero absorption.

In view of the application of different marker materials, as described above, the source assembly 8 of the present system is preferably provided with a first radiation source 8a configured to provide a first type of illumination radiation L1 (see FIG. 1) to enable the device 1 to detect the first marker material, and a second radiation source 8b configured to provide a second type of illumination radiation L2 (see FIG. 2) to enable the device 1 to detect the second marker material. For example, each of the first and second source 8a, 8b can be a laser, an incandescent lamp, or a different type of radiation source. Particularly, the second type of illumination radiation differs from the first type of illumination radiation in one or more of: wavelength, wavelength spectrum, and spectral bandwidth. Preferably, the radiation sources 8a, 8b can be controlled independently, for example activated and deactivated at desired times, by the controller 9. According to an embodiment, during operation, only one of the first and second type of radiation L1, L2 is directed onto the sample S at a time.

The first and second source 8a, 8b can be separate entities, as depicted, or they can be integrated with each other. In case of separate radiation sources 8a, 8b, a radiation directing unit 9 can be provided (for example including a controllable, movable mirror, or a suitable beam combiner) to direct the radiation from each of the sources 8a, 8b into an optical path leading to the sample S (which path is via the beam splitter 5 and objective lens unit 3 in the present system).

Alternatively, there can be provided a single radiation source 8 configured to emit broad-band spectrum radiation of to emit radiation of a predetermined part of the spectrum, the single radiation source being provided with a controllable radiation filter to adjust the spectrum of radiation emitted thereby. For example, the radiation source filter can be configured to be controlled to provide a first filter mode, to block one or more predetermined radiation spectrum bands from radiation emitted by the source to provide the first type of illumination radiation, and to provide a second filter mode to transmit that one or more predetermined radiation spectrum bands to provide the second type of illumination radiation.

As is mentioned above, radiation L1 used in the focusing step can be specifically suitable to interact with the first marker material in order to detect the first marker material. Radiation L2 used in the imaging step can be chosen to interact with the second marker material to detect that second marker material.

Preferably, radiation L1 emitted by the first source 8a has a different spectrum than radiation L2 emitted by the second source 8b. Also, the spectrum of the first type of radiation can partly overlap with the spectrum of the second type of radiation L2, depending on the marker materials.

In a further embodiment, the first type of illumination radiation (emitted by a first radiation source 8a) does not degrade the above-mentioned second marker material. In an embodiment, however, the second type of illumination radiation can lead to degradation of the second marker material. This can be the case when the second marker material is a fluorescent material (since such material can be photobleached by illumination of certain wavelengths). For example, said degradation can be one or more of: changing optical properties of the respective material, a reduction of the amount of the material, a photobleaching of the material, and/or a different type of degradation.

Preferably, the above-mentioned radiation detector 4 is arranged to detect a first type of sample radiation E1 (i.e. radiation emanating from the sample), relating to the first marker material, and arranged to detect a second type of sample radiation E2 relating to the second marker material.

Also, the controller 6 can be configured to process imaging data obtained by the imaging device 1 (due to the detector 4 detecting the first type of sample radiation E1) in a focusing step to determine at least one in-focus position of the imaging device 1 with respect to the sample S. The controller 6 can be adapted to control the imaging device 1 to attain said in-focus position for carrying out at least one subsequent imaging step.

During operation, the above-described system can be used in a method for imaging samples, the method at least comprising an afore-mentioned staining of a sample with a first marker material and with a second marker material. Then, as is indicated in FIG. 1, the first marker material (present in the sample, for example to mark certain sample parts M) is used in a focusing step for focusing the imaging device 1 with respect to the sample S (or sample part) to an in-focus position. To that aim, the sample S is irradiated using a suitable first type of radiation L1, leading to a first type of sample radiation E1 emanating from the sample S, which sample radiation E1 is detected by the detector 4. The irradiation can be a continuous sample irradiation, a semi-continuous irradiation, a pulse-like irradiation, or differently, using a suitable radiation dose that results in sufficient sample radiation E1 for detection thereof. Besides, the device 1 can be configured to adjust the radiation dose during the focusing step, for example in the case that the detector 4 detects insufficient or excessive amounts of sample radiation E1.

The focusing step can involve obtaining and storing resulting device focusing information, to be used in one or more (subsequent) imaging steps.

Also, the focusing step can involve adjusting the position of the sample S with respect to the lens unit 3 (in Z direction) to determine which position(s) is/are (an) in-focus position(s) with respect to one/several sample parts M.

In a further embodiment, the sample S can also be scanned in one or more directions orthogonal to the Z-direction, with respect to the lens unit 3, for example to direct the focusing beam to different (spaced-apart) sample parts M. One or more focusing steps can be carried out, for example to obtain device in-focus information regarding several parts M of the sample S.

During the focusing step, the sample S can be irradiated to detect the first marker material, using a first type of radiation L1 (in the present embodiment provided by the first source 8a) that does not degrade the second marker material. For example, in case the first marker material is Eosin Y and the second marker material is DAPI, the first type of radiation L1 preferably has no spectrum parts around the absorption peak (about 360 nm) of DAPI. In that case, the first type of radiation L1 is configured to excite Eosin Y (for example using single-photon excitation), for example by including spectrum parts at 525 nm (leading to gradual degradation of the Eosin Y marker).

Figure 3:
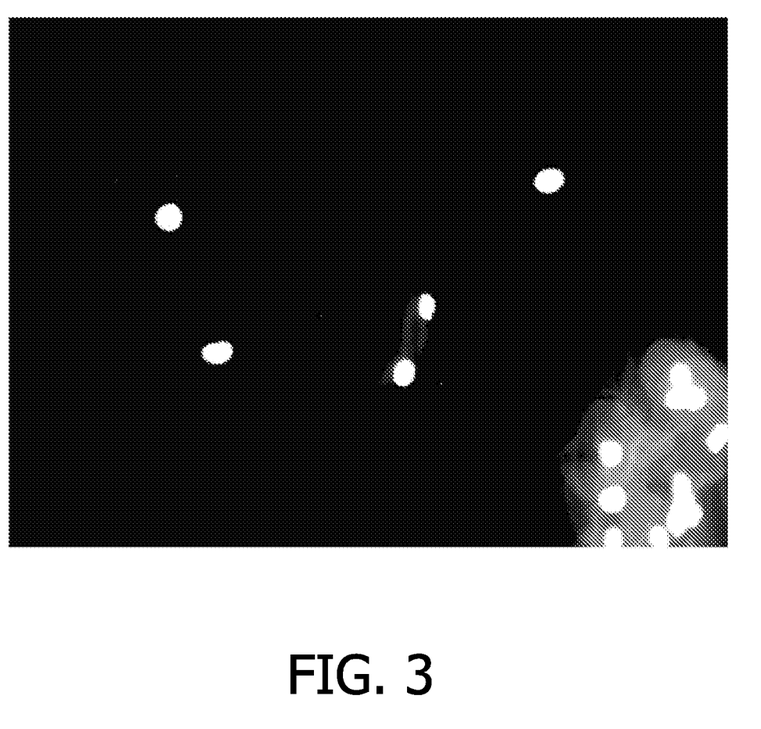
FIG. 3 shows an example of an image obtained with the system of FIG. 1.

Then (after desired in-focus information has been obtained), the imaging device 1 can be focused with respect to the sample S, at least, be brought to at least one mentioned in-focus position, see FIG. 2. Then, the second marker material (present in the sample) is used in one or more imaging steps, wherein the imaging device 1 acquires at least one image of the sample (or sample part M). To that aim, the sample S is irradiated to detect the second marker material, using the second type of radiation L2. An example of a resulting image, in case of fluorescence imaging during the imaging step, is shown in FIG. 3. Particularly, FIG. 3 shows a fluorescence image of a sample section having a plurality of cells being marked by a suitable fluorophore (bright).

Also, during the imaging step, the irradiation can be a continuous sample irradiation, but is preferably a semi-continuous or a pulse-like irradiation, using a suitable radiation dose to provide sufficient sample radiation E2 for detection thereof.

During the imaging step the sample S can be irradiated with the second radiation L2 (in the present embodiment provided by the second source 8b), leading to a second type of sample radiation E2 emanating from the sample to be detected by the detector 4.

Preferably, during the imaging step, each exposure time is controlled and fixed. Preferably, each illumination radiation dose (for example measured in Rad (radiation absorbed dose)) used during an imaging step is constant (equal) for each image to be acquired (i.e., the same dose of the second radiation L2 is used to acquire each image of a multitude of images). Besides, the device 1 can be used to image several (different) samples S, for example in a sequence, by replacing the sample holder H of an imaged sample S with new holder holding a subsequent sample to be imaged. In that case, preferably, the same radiation dose of the second type of radiation L2 is applied to each of the samples during their respective imaging steps.

For example, in case the first marker material is Eosin Y and the second marker material is DAPI, the second type of radiation L2 is configured to excite DAPI, for example by including spectrum parts at 360 nm (implicitly leading to gradual degradation of the DAPI marker).

Preferably, an imaging step involves illuminating the sample S with the second radiation type L2 during a relatively short predetermined (preferably fixed) time period, for example a period of about 10 seconds or less, particularly 1 second or less, for example during a fraction of a second, for each image to be taken.

Preferably, during operation, the imaging device 1 automatically carries out a self-focusing onto the sample S and the imaging of the sample, utilizing the first and second marker materials. A device auto-focus procedure, including image data processing to obtain desired in-focus positions (between sample S or sample parts and the imaging device), adjusting the position of the sample S with respect to the lens unit 3 (via actuator 7), radiation source operation activation/deactivation) and other device functions can be controlled by the controller 6, as will be appreciated by the skilled person.

In a further embodiment the method can include determining a plurality (for example sequence) of in-focus positions, for example relating to different sample parts M, as part of the focusing step, leading to in-focus information containing those in-focus positions. The resulting in-focus information can then be used in an imaging sequence, involving the focusing of the imaging device 1 with respect to the sample S (or sample part M) to each in-focus position and to obtain the image of the sample S (or sample part M) at the respective in-focus position. Alternatively, different sample parts M can be imaged subsequently, using a respective focusing step and respective imaging step for one sample part to be imaged, before application of a focusing step and respective imaging step for a next sample part.

For example, in an embodiment, sample images obtained by the present method can be used to provide a final DNA cytometry histogram, as will be appreciated by the skilled person.

As follows from the above, in various embodiments of the present invention, a different technique is used for focusing the sample S, preferably using a light source 8a that does not bleach fluorophores (i.e. markers), and consecutively expose the sample S to the excitation light for a fixed and controlled time slot, which is preferably sufficient to collect a fluorescence picture.

Embodiments can apply two imaging modes: in a focusing mode, light is used that does not affect a fluorophore to be measured but is used to bring tissue samples S to a right focusing position, and in an imaging mode two for a brief moment in time the light affecting the fluorophore is switching on for the DNA-cytometry measurement and directly switched off afterwards. Preferably, the exposure time is controlled and fixed, such that a residual photobleaching is the same for all exposed sample parts (for example cells) in a final DNA cytometry histogram, which can be obtained with the imaging results, and thus it will not affect the measurement Coefficient of Variance (CV). Additionally, the exposure time of the fluorophore used for the DNA-cytometry measurement can be minimized to the time that is necessary to take a picture (i.e. in the order of seconds or less), the photobleaching is strongly reduced.

In a further embodiment, a plurality of sample images at different z-positions (i.e. different positions along the Z-direction) can be taken by the imaging device 1. The resulting images can then be used in a focusing step or mode to find out in which image which cell is in focus, and use than the image in the imaging step or mode for this z-position to measurement for the DNA-cytometry. In this way, a good DNA-cytometry measurement can be obtained, wherein each cell can be in focus, receiving the same amount of exposure (radiation dose), in order to correctly quantitatively measure the amount of fluorescence from the cell nucleus. This is particularly advantageous in combination with multi-photon excitation (see below).

As follows from the above, an option is to use fluorescence imaging in both modes, by staining the sample S with two different dyes: one for the focusing mode, and another for the actual DNA-cytometry method (for instance DAPI), such that the dye used for that imaging mode is excited at a significantly different wavelength than the dye in the focusing mode. Hence by applying first a wavelength that excites the fluorophore in the focusing mode and not in the imaging mode, the sample S can be brought in focus. That the first marker (fluorophore) bleaches in the focusing mode is not a problem because it is not used for quantitative measurement. Once in focus, radiation L2 having another wavelength can be used to excite the second marker fluorophore, to do an DNA-cytometry measurement.

A further embodiment includes application of scanning confocal microscopy. In addition to the above embodiment, the focusing step can include scanning, and bringing one or more cells of interest in focus. Then, during the imaging step, the cells M of interest can be scanned again, for the DNA-cytometry method, in which case the confocal illumination is only activated during a scanning of the desired cell, and is not active when the device scans outside the cell(s) M of interest. In this way, during the scan, other cells that still have to be measured are not illuminated in the imaging step and hence do not yet suffer from bleaching.

Embodiments of the invention can enable fast DNA-cytometry based cancer detection (minutes instead of hours in the conventional Fuelgen stained DNA-cytometry method). Application areas are now for instance surgical support tool for cancer boundary detection during cancer tissue resections.

Although the illustrative embodiments of the present invention have been described in greater detail with reference to the accompanying drawings, it will be understood that the invention is not limited to those embodiments. Various changes or modifications may be effected by one skilled in the art without departing from the scope or the spirit of the invention as defined in the claims.

It is to be understood that in the present application, the term "comprising" does not exclude other elements or steps. Also, each of the terms "a" and "an" does not exclude a plurality. Any reference sign(s) in the claims shall not be construed as limiting the scope of the claims.

For example, in the present application, one or both of the focusing step and imaging step can include single photon excitation of fluorescent marker material (see above). In that case, absorption of single photons of illumination radiation provides energy to excite the respective fluorescent material.

Alternatively, one or both of the focusing step and imaging step can include multi-photon excitation of fluorescent marker material, for example 2-photon excitation, known as such from the prior art (see for example U.S. Pat. No. 7,170,675). In that case, absorption of multiple (for example 2) photons provides energy equivalent to a single-photon excitation to excite fluorescent material. Application of this type of excitation of marker material is particularly advantageous in case of taking plurality of sample images at different Z-positions (along the direction Z). Particularly, the multi-photon (2-photon) excitation of marker material generally requires relatively high photon densities, which high densities can be obtained at instantaneous in-focus positions (for example using a high power excitation laser source) of the imaging device 1. Instantaneous out-of-focus positions (i.e. instantaneous Z-positions other than an in-focus Z-position) will receive lower photon densities, which lower densities will not lead to (or considerably reduce chances to) excitation of the respective marker material (at respective instantaneous out-of focus position). Therefore, both the focusing step and imaging step preferably include multi-photon excitation (of respective first and second fluorescent marker materials) in case of taking plurality of sample images at different Z-positions.

Besides, in this application, radiation can involve photon radiation, particle beam radiation, or a different type of radiation. Besides, for example, fluorescent markers can be configured to be attached to certain molecules. These markers can be characterized in that they attach themselves very specifically to, for example, certain types of antibodies, without attaching themselves to other types of antibodies and other molecules. Furthermore, these markers can be characterized in that, in response to excitation by, for example, photons, they emit fluorescence radiation E1, E2. For example, a marker can be an organic or inorganic marker. Organic markers generally comprise aromatic rings. Examples are FITC (fluorescein isothiocyanate), TRITC (tetramethylrhodamine isothiocyanate) and DAPI. Many types of organic markers are commercially available, each with its own attachment properties. Such organic markers are sold nowadays by, for example, the firm Molecular Probes, Inc., Eugene, Oreg., USA.

The invention claimed is:

1. A method for imaging samples, at least comprising:
    staining of a sample with a first marker material and with a second marker material;
    utilizing the first marker material in a focusing step for focusing an imaging device with respect to the sample; and
    utilizing the second marker material and the imaging device, which has been focused in the focusing step, in an imaging step to acquire an image of the sample,
    wherein the sample is irradiated to detect the first marker material, in the focusing step, using a first type of radiation that does not degrade the second marker material, wherein the sample is irradiated to detect the second marker material, in the imaging step, using a second type of radiation that degrades the second marker material, and wherein the first marker material and second marker material are designed to tag the same sample component or sample structure.

2. A method according to claim 1, wherein optical properties of the second marker material differ from optical properties of the first marker material.

3. A method according to claim 1, wherein at least the second marker material is a fluorescent marker material.

4. A method according to claim 3, wherein the first marker material and second marker material are fluorescent markers, having different fluorescent properties.

5. A method according to claim 1, wherein the first marker material and second marker material are designed to tag one or more of a molecule, nucleic acid, DNA, RNA, antibody, cell, membrane, cell part, protein, tissue, and biologic material.

6. A method according to claim 1, wherein the focusing step and the imaging step involve irradiation of the sample with suitable radiation, and detection resulting sample radiation emanating from the sample using a radiation detector of the imaging device.

7. A method according to claim 1, wherein the imaging device automatically carries out a self-focusing onto the sample and the imaging of the sample, utilizing the first and second marker materials.

8. A method according to claim 1, wherein the wavelength of a main radiation absorption peak of the first marker material is higher than the wavelength of a main radiation absorption peak of the second marker material.

9. A sample imaging system, the system comprising an imaging device configured to image samples and a focusing unit configured to focus the imaging device onto samples to be imaged, the system including a controller that is configured to control the system to carry out the focusing and imaging steps of the method according to claim 1.

10. A system according to claim 9, wherein the focusing unit is integrated with the imaging device.

11. A system according to claim 9, comprising a first radiation source configured to provide a first type of illumination radiation that does not degrade the second marker material, and a second radiation source configured to provide a second type of illumination radiation that degrades the second marker material.

12. A system according to claim 9, the imaging device comprising a radiation detector arranged to detect a first type of sample radiation, emanating from the sample, relating to the first marker material, and arranged to detect a second type of sample radiation relating to the second marker material.

13. A system according to claim 9, wherein the controller is configured to process imaging data obtained by the imaging device in the focusing step to determine at least one in-focus position of the imaging device with respect to the sample, wherein the controller is adapted to control the imaging device to attain said in-focus position for carrying out the imaging step.

14. A sample imaging system, the system comprising:
    means for staining of a sample with a first marker material and with a second marker material;
    means for utilizing the first marker material in a focusing step for focusing an imaging device with respect to the sample; and
    means for utilizing the second marker material and the imaging device, which has been focused in the focusing step, in an imaging step to acquire an image of the sample,
    wherein the sample is irradiated to detect the first marker material, in the focusing step, using a first type of radiation that does not degrade the second marker material, wherein the sample is irradiated to detect the second marker material, in the imaging step, using a second type of radiation that degrades the second marker material, and wherein the first marker material and second marker material are designed to tag the same sample component or sample structure.

* * * * *